United States Patent [19]

Slump

[11] Patent Number: 5,040,201
[45] Date of Patent: Aug. 13, 1991

[54] X-RAY EXPOSURE SYNCHRONIZATION METHOD AND APPARATUS

[75] Inventor: Cornelis H. Slump, Eindhoven, Netherlands

[73] Assignee: U.S. Philips Corporation, New York, N.Y.

[21] Appl. No.: 527,998

[22] Filed: May 22, 1990

[30] Foreign Application Priority Data

May 26, 1989 [NL] Netherlands .......................... 8901322

[51] Int. Cl.$^5$ ............................................. H05G 1/10
[52] U.S. Cl. .......................................... 378/95; 378/91
[58] Field of Search ...................................... 378/95, 91

[56] References Cited

U.S. PATENT DOCUMENTS 3,871,360  3/1975  Van Horn et al. .................... 378/95

OTHER PUBLICATIONS

C. H. Slump, May 25-26, 1989, pp. 125-131, "On the Prediction of the Optimal Exposure Timing from ECG Data in Digital Subtraction Angiograph (DSA)".
DVI-V The Master Touch in DSA-Philips Brochure, 1/85.

Primary Examiner—Craig E. Church
Attorney, Agent, or Firm—William Squire

[57] ABSTRACT

A periodically moving object, e.g., the heart, is X-rayed in response to periodic pulses generated at instances in the period at which the object is anticipated to be in a given position. Stochastic movements shift the position of the object at those instances such that image artifacts may result. A prediction methodology is utilized to predict when the object has moved stochastically and therefore will be out of position at the forthcoming pulse. That forthcoming pulse is then suppressed to preclude imaging the object out of position. Kalman filtering is utilized in the prediction methodology.

5 Claims, 2 Drawing Sheets

X-RAY EXPOSURE SYNCHRONIZATION METHOD AND APPARATUS

FIELD OF THE INVENTION

The invention relates to an X-ray exposure synchronisation method for making time sequential X-ray images of a periodically moving object, the object being irradiated by an X-ray beam emitted by an X-ray source, a recording device measuring a movement period of the object and recording pulses being applied to a synchronisation device which activates and de-activates the X-ray source.

BACKGROUND OF THE INVENTION

The invention also relates to a device comprising an X-ray source, a recording device and a synchronization device suitable for carrying out the X-ray exposure synchronization method. An X-ray exposure synchronization method and a device of this kind are known from the leaflet "Philips Medical Systems", 4522 984 09241/744, DVI-V, January 1985.

During the formation of an X-ray image of an object in, for example a human body, for example a heart or blood vessel, the X-ray beam is attenuated by the object and its environment. In a human body the object to be imaged and its environment consist mainly of water, so that the X-ray beam is attenuated to substantially the same extent by the object and its environment. This results in a low-contrast image of the object. By filling the object to be imaged with a contrast agent having a comparatively high X-ray absorption, such as iodide, and by subtracting an image of the object filled with contrast agent from an image of the object recorded without contrast agent, i.e. a so-called mask image, contrast enhancement is achieved If the image of the object filled with contrast agent has been shifted with respect to the mask image due to movement of the object, artefacts will occur in the contrast-enhanced image. Notably during the formation of a series of successive X-ray images which are summed for noise integration prior to display on a television monitor, or which follow a flow of contrast agent through the object to be imaged, contrast enhancement by subtraction from a mask image will be strongly degraded by movement of the object. For the imaging of vessels situated in the vicinity of a heart, the problems will occur due to cardiac movement. By measuring a movement rhythm of an object by means of the recording device, for example the formation of an electrocardiogram, exposure can be synchronized with the movement rhythm. This takes place, for example in the Philips DVI-V system. Because the exposure is performed after a predetermined delay with respect to a recording pulse supplied by the recording device, the X-ray images are in phase and register with the mask image. This has a drawback in that in the event of fluctuations of the movement rhythm of the object to be imaged, caused, for example by the contrast agent, the X-ray images will show the object in different positions, so that artefacts will occur still when this X-ray exposure synchronisation method is used.

SUMMARY OF THE INVENTION

The invention has inter alia for its object to provide an X-ray exposure synchronization method in which the occurrence of movement artefacts is reduced.

To achieve this, an X-ray exposure synchronization method in accordance with the invention wherein an instant of a forthcoming recording pulse is calculated from the recording pulses by means of arithmetic means in the synchronization device.

Calculation of the instant of the forthcoming recording pulse from the measured recording pulses enables exposure to take place at a constant instant in time between two successive recording pulses, that is to say in a constant object position. Variations in the movement rhythm are detected by the calculation and the synchronization of the X-ray source is adapted to the changed movement rhythm. As the effect of recording pulses which are more distant in time is made stronger or weaker in the calculation, the synchronization responds more quickly or less quickly to rhythm variations. When the object movement exhibits stochastic movements in addition to the systematic accelerations and decelerations, for example, additional systoles or premature ventricular contractions of a heart, the recording pulses will not succeed one another at exactly predictable instants. For accurate calculation of the forthcoming recording pulse by combination of the measured recording pulses, it is essential that the preceding pulses are correctly weighted so that not every fluctuation causes a variation of the synchronization, without the synchronization becoming insensitive to systematic rhythm variations. When the mean movement rhythm and the variance are characterising parameters of the stochastic process describing the objection motion, an accurate prediction of the forthcoming recording pulse can be made when the mean value and the variance are known. Usually, there is no time for an extensive statistic analysis of the object movement and a number of X-ray images must be quickly formed because of the displacement of contrast agent. The calculation should generate a value for the instant of the forthcoming recording pulse within a mean period of the recording pulses, so that it should require little calculation time. A calculation of the forthcoming recording pulse should also be fully automatic in order to simplify the formation of X-ray images.

A preferred version of an X-ray exposure synchronization method in accordance with the invention is characterized in that a recursive Kalman filter method is used for calculating the forthcoming recording pulse.

The use of a Kalman filter method results in a recursive description of the movement rhythm, which description adapts itself to variations of this stochastic process. This calculation method adequately distinguishes non-systematic variations of the movement rhythm from systematic variations. This is advantageous notably for cardiologic angiographic examinations.

BRIEF DESCRIPTION OF THE DRAWINGS

The invention will be described in detail hereinafter with reference to the accompanying drawing. Therein:

FIGS. 2a to 2f show series of recording pulses with associated synchronization pulses.

DESCRIPTION OF PREFERRED EMBODIMENTS

Figure 1:
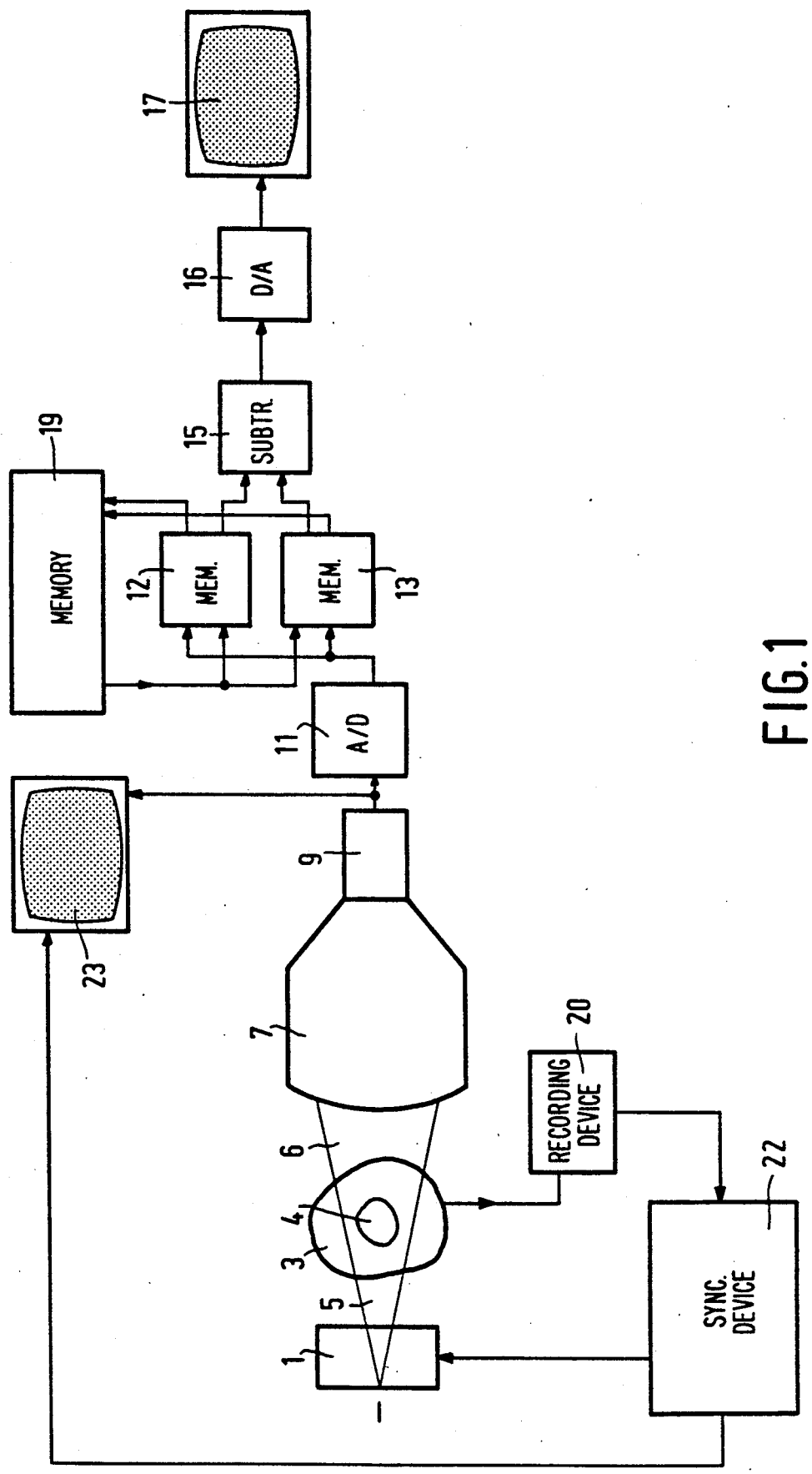
FIG. 1 diagrammatically shows a device suitable for carrying out the X-ray exposure synchronization method.

FIG. 1 shows an X-ray source 1 which irradiates an object 3, containing a detail 4, by means of an X-ray beam 5. Using an X-ray detector 7, in this case an X-ray intensifier tube, an image carrying X-ray beam 6 is converted into an optical image which appears on an exit screen of the X-ray image intensifier tube and which is converted into an electric signal by means of a television camera tube 9. This signal is applied to an analog-to-digital converter 11 and subsequently to one of the memories 12 or 13. For example, in the memory 12 an image of the object 3 containing a detail 4 filled with contrast agent is stored and in the memory 13 a mask image of the object 3 is stored. After logarithmation of the signals in the memories 12 and 13, the digital images in the memories are subtracted in a subtraction device 15, thus producing a contrast-enhanced image of the detail 4. After digital-to-analog conversion by means of a digital-to-analog converter 16, this image is displayed on a monitor 17. The digital X-ray images stored in the memories 12 and 13 can be stored in a background memory 19 wherefrom digital images can also be applied to the memories 12 and 13. In order to determine a movement rhythm of the detail 4, a recording device 20 is connected to the detail 4, which recording device applies a pulse-shaped signal to a synchronization device 22 at instants at which the detail 4 occupies a predetermined position. The synchronization device 22 calculates the instant of the forthcoming recording pulse from the recording pulses and detects systematic rhythm variations of the detail 4. The synchronization device 22 activates the X-ray source 1 in synchronism with a frame period, for example 40 ms, of a television monitor 23 displaying a real-time image of the object.

Figure 2A:
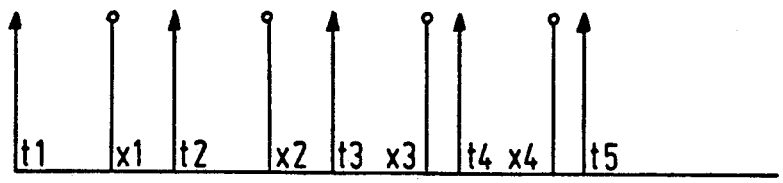
Figure 2B:
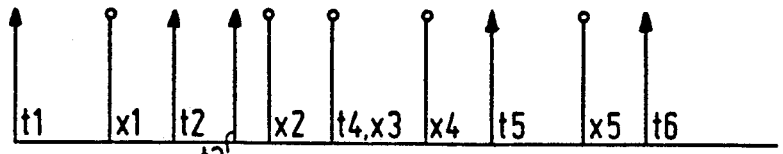
Figure 2C:
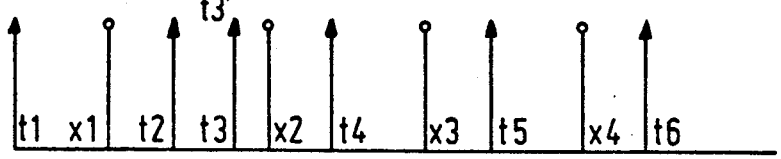
Figure 2D:
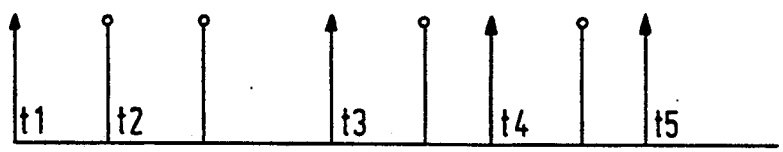
Figure 2E:
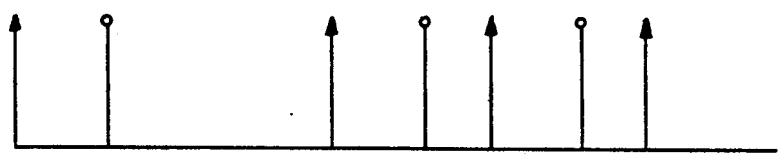

FIG. 2a shows a series of recording pulses $t_1$-$t_5$ which succeed one another with an interval T, a systematic rhythm variation occurring after the instant $t_3$. Synchronization of the X-ray source by the synchronization device at the instants $x_1$-$x_4$, delayed a given period of time with respect to the recording pulses, takes place at instants preceding the rhythm variation at a fraction of T which deviates from the fraction of T after the rhythm variation. By calculating the forthcoming interval T and by effecting the synchronization at a predetermined fraction of T after the last recording pulse, the described problem is avoided. FIG. 2b shows a stochastic rhythm variation which occurs in heart rhythms: the extra systole. In that event an additional heart contraction occurs between two heart beats which succeed one another with an interval T. Synchronization after a time delay, predetermined with respect to the last recording pulse, leads to an out-of-phase exposure at the instants $x_2$ and $x_3$. FIG. 2c shows that, if the fluctuation does not have any effect on the calculated forthcoming recording pulse, out-of-phase exposure takes place only at the instant $x_2$. By recognizing the recording pulse $t_3$ as a stochastic fluctuation, the synchronization at the instant $x_2$ can be suppressed on the basis thereof. A further fluctuation occurring in a heart rhythm is a so-called premature ventricular contraction, where one recording pulse appears earlier and where the subsequent recording pulse appears at the expected instant. In that case out-of-phase exposures occur at the instants $x_1$ and $x_2$ according to the known synchronization method, out of phase exposure taking place exclusively at the instant $x_1$ when use is made of the synchronization in accordance with the invention. Synchronization at the instant $x_2$ can be suppressed after recognition of the recording pulse $t_2$ as a stochastic fluctuation.

Figure 3:
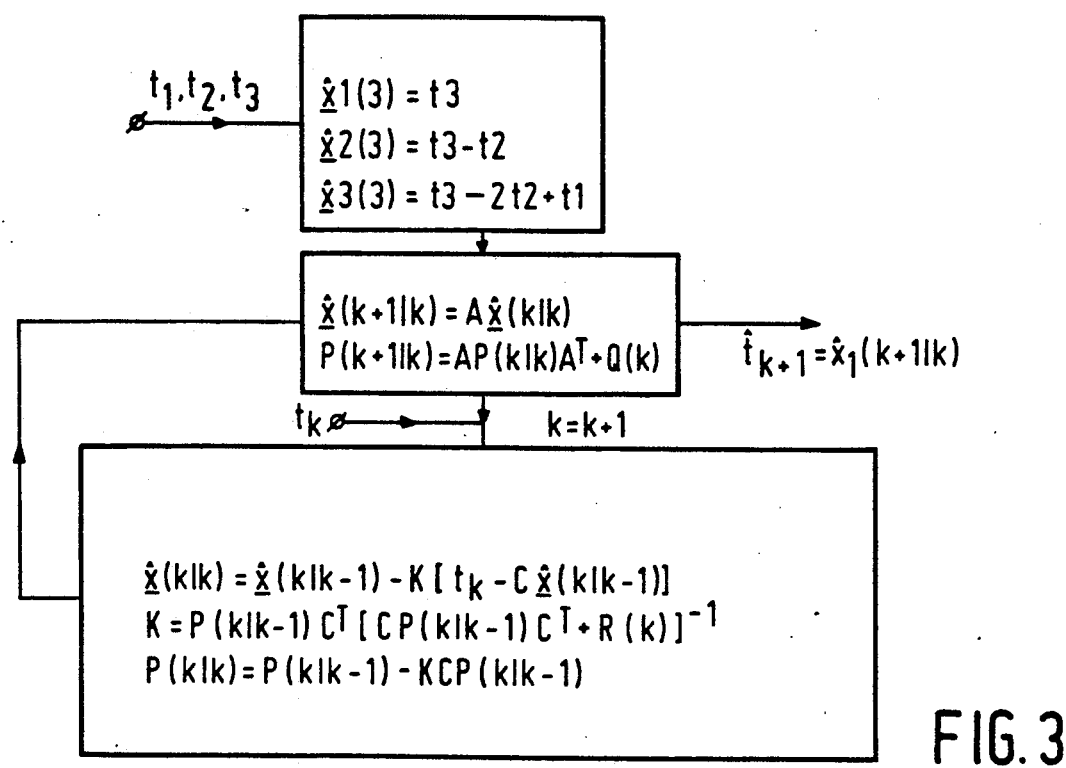
FIG. 3 shows a flowchart of a calculation method for the forthcoming recording pulse according to the Kalman filter method.

FIG. 3 shows a flowchart for the Kalman filter method. For a mathematical description of the problem of predicting the movement rhythm of the object to be imaged, the movement rhythm is represented as a stochastic process, a three dimensional vector x(t) of which comprises the parameters relevant to the process. It has been that found that $x_1(t_n)=t_n$, $x_2(t_n)=t_n-t_{n-1}$ and $x_3(t_n)=t_n-2t_{n-1}+t_{n-2}$ adequately characterize the process. The process is represented by the relation:

$$x(k+1) = Ax(k) + w(k) \tag{1}$$

Therein, the bars denote column vectors and a capital letter denotes a matrix. w (k) is represented as a stochastic white process with a mean zero:

$$E[w(k) \cdot w^T(l)] = Q(k)\sigma_{k,l} \tag{2}$$

Therein, E is the predictor operator and w $(k)^T$ is the transposed vector of the column vector w (k).

The first-order autoregressive process as described equation 1 is observed as a series of discrete measurements y (k), the recording pulses, which are related to the system by:

$$y(k) = Cx(k) + v(k) \tag{3}$$

Therein, C=(1,0,0) and v (k) is a white noise disturbing the measurement values, with a mean zero and with a covariance matrix:

$$E[v(k) \cdot v(l)] = R(k)\sigma_{k,l} \tag{4}$$

Furthermore, w (k) and v (k) are non-correlated. The problem to be solved consists in that the movement rhythm x(k+1) must be calculated from the recording pulses y(0) ... y(k) observed. This predictor is denoted as x(k+1|k), where $x(k+1|k)=E[x(k+1)|y(k)]$, being the conditional mean value of x(k+1) for y(k) given. Because x(k) and y(k) together have a gaussian distribution, the statistics of the movement rhythm is described fully by the conditional mean and the variance of this distribution. The common conditional probability distribution is recursively given by the Kalman filter method. The Kalman filter method minimizes the mean squared error in the predicted forthcoming recording pulse $E[(t_{n+1}-t_n)^2]$. For x (k+1|k) the Kalman filter method produces:

$$\hat{x}(k+1|k) = Ax(k|k-1) + G(k)[y(k) - Cx(k|k-1)] \tag{5}$$

or $$\hat{x}(k+1|k) = Ax(k|k) \tag{5b}$$

Therein, G(k) is the predictor gain matrix. G(k) is given by:

$$G(k) = AP(k|k-1)C^T[CP(k|k-1)C^T + R(k)]^{-1} \tag{6}$$

The Kalman gain matrix K(k) is defined as:

$$AK(k) = G(k) \tag{6b}$$

P(k+1|k) is the predicted mean squared error matrix:

$$P(k+1|k) = (A - G(k)C)P(k|k-1)A^T + Q(k) \quad (7)$$

The mean squared error matrix $P(k|k)$ is:

$$P(k|k) = E[(x(k) - x(k))(x(k) - x(k))^T] \quad (8)$$

For the described application:

$$A = \begin{pmatrix} 1 & 1 & 1 \\ 0 & 1 & 1 \\ 0 & 0 & 1 \end{pmatrix}$$

It is assumed that:

$$R(k) = 0.5 \text{ and } Q(k) = \begin{pmatrix} 0.5 & 0 & 0 \\ 0 & 1 & 0 \\ 0 & 0 & 2 \end{pmatrix}$$

The initialisation is:

$$x_1(3) = t_3$$

$$x_2(3) = t_3 - t_2, \text{ and}$$

$$x_3(3) = t_3 - 2t_2 + t_1.$$

For $P(3|3)$ the initialization is:

$$P(3|3) = \begin{pmatrix} 0.5 & 1 & 2 \\ 1 & 1 & 1 \\ 2 & 1 & 2 \end{pmatrix}$$

From (5) it follows for the predicted value of x that:

$$x(4|3) = Ax(3|3) = 3(t_3 - t_2) + t_1$$

and from (7) it follows for the predicted value of P that:

$$P(4|3) = AP(3|3)A^T + Q(k)$$

A correction is required at the next instant:

$$x(4|4) = x(4|3) + K(k)(y(4) - Cx(4|3)) \quad (9)$$

with K the Kalman gain matrix:

$$K(k) = P(4|3)C^T(CP(4|3)C^T + 0.5)^{-1} \quad (10)$$

$P(4|4)$ is given by:

$$P(4|4) = P(4|3) - KCP(4|3) \quad (11)$$

After elaboration of equations 9, 10 and 11, $x(5|4)$ can be calculated by means of equation 5 etc.

What is claimed is:

1. An X-ray exposure method for making time-sequential X-ray images of a periodically moving object which occasionally tends to move stochastically causing an artifact in at least one of said images comprising:
   determining the movement period of the object;
   generating pulses manifesting a predetermined position of said object at the instances of the boundaries of said period;
   irradiating the object with an X-ray beam in response to said pulses; and
   predicting the time of occurrence of a pulse at the instant of a forthcoming boundary of said period, the predicting including recursive filtering with a Kalman filtering method.

2. The method of claim 1 further including suppressing the generation of a pulse at said instant of the forthcoming boundary to thereby preclude the generation of said artifact.

3. An X-ray exposure method as claimed in claim 2 including describing the predetermined object position as a function of time by a three-dimensional vector, elements of which are determined from three successive pulses $t_n$, $t_{n-1}$ and $t_{n-2}$, a first element having a value $t_n$; a second element having a value $t_n - t_{n-1}$, and a third element having a value $t_n - 2t_{n-1} + t_{n-2}$.

4. An X-ray exposure apparatus for making time-sequential X-ray images of a periodically moving object which occasionally tends to move stochastically causing an artifact in at least one of said images comprising:
   means for determining the movement period of the object;
   means responsive to said means for determining for generating pulses manifesting a predetermined position of said object at the instances of the boundaries of said period;
   means for irradiating the object with an X-ray beam in response to said pulses; and
   means for predicting the time of occurrence of a pulse at the instant of a forthcoming boundary of said period, said latter means including means for recursive filtering with a Kalman filtering method.

5. The apparatus of claim 4 further including means responsive to said means for predicting for suppressing the generation of a pulse at said instant of the forthcoming boundary to thereby preclude the generation of said artifact.

* * * * *